United States Patent
Amon

(10) Patent No.: US 8,156,440 B2
(45) Date of Patent: Apr. 10, 2012

(54) USER INTERFACE FOR A DICOM TRANSFER CONFIGURATION

(75) Inventor: Franz Amon, Hessdorf (DE)

(73) Assignee: Siemens Aktiengesellschaft, Munich (DE)

( * ) Notice: Subject to any disclaimer, the term of this patent is extended or adjusted under 35 U.S.C. 154(b) by 806 days.

(21) Appl. No.: 11/937,296

(22) Filed: Nov. 8, 2007

(65) Prior Publication Data

US 2009/0125816 A1     May 14, 2009

(51) Int. Cl.
*G06F 3/00* (2006.01)

(52) U.S. Cl. .......................... 715/748; 715/772

(58) Field of Classification Search ............... 715/807, 715/810, 772, 748
See application file for complete search history.

(56) References Cited

U.S. PATENT DOCUMENTS

| | | | |
|---|---|---|---|
| 6,331,776 B1 * | 12/2001 | Debbins et al. | 324/309 |
| 6,388,687 B1 * | 5/2002 | Brackett et al. | 715/810 |
| 6,424,996 B1 * | 7/2002 | Killcommons et al. | 709/206 |
| 6,603,494 B1 * | 8/2003 | Banks et al. | 715/807 |
| 6,609,217 B1 * | 8/2003 | Bonissone et al. | 714/26 |
| 7,280,702 B2 | 10/2007 | Chang et al. | |
| 2002/0023172 A1 * | 2/2002 | Gendron et al. | 709/238 |
| 2002/0063560 A1 * | 5/2002 | Debbins et al. | 324/307 |
| 2002/0140725 A1 * | 10/2002 | Horii | 345/736 |
| 2004/0230613 A1 * | 11/2004 | Goldstein et al. | 707/104.1 |
| 2006/0095423 A1 * | 5/2006 | Reicher et al. | 707/3 |
| 2006/0168338 A1 * | 7/2006 | Bruegl et al. | 709/240 |
| 2006/0242148 A1 * | 10/2006 | Rothpearl et al. | 707/7 |
| 2006/0282302 A1 * | 12/2006 | Hussain | 705/9 |
| 2007/0043535 A1 * | 2/2007 | Belden | 702/183 |
| 2007/0118635 A1 * | 5/2007 | Nakano | 709/223 |
| 2007/0167724 A1 * | 7/2007 | Gadagkar et al. | 600/410 |
| 2007/0203748 A1 | 8/2007 | Rothpearl et al. | |
| 2007/0299945 A1 * | 12/2007 | Lunsford | 709/223 |
| 2008/0140448 A1 * | 6/2008 | Hernandez et al. | 705/2 |
| 2009/0080721 A1 * | 3/2009 | Yan et al. | 382/128 |

* cited by examiner

*Primary Examiner* — Weilun Lo
*Assistant Examiner* — Enrique Iturralde
(74) *Attorney, Agent, or Firm* — Lempia Summerfield Katz LLC

(57) ABSTRACT

A graphic user interface as well as related methods and logic for a DICOM transfer configuration are provided. For example, a first image object corresponding to an origin node is provided. A second image object corresponding to a destination node is provided. The second image object includes an indicator associated with a DICOM transfer. At least one link image object is between the first image object and the second image object. The link image object is indicative of a potential DICOM transfer. The first, second, and link image objects are displayed in a user interface. The potential DICOM transfer is operable to be configured via the user interface.

23 Claims, 3 Drawing Sheets

USER INTERFACE FOR A DICOM TRANSFER CONFIGURATION

BACKGROUND

The present embodiments relate to data communication. In particular, medical data transfers are configured.

Medical imaging and applications are utilized for research, treatment, and other professional purposes. Sharing of medical data between physicians or entities allows for greater medical care and progress. For example, digital imaging and communications in medicine ("DICOM") is a standard for storing, printing, and transmitting medical information. DICOM includes a network communications protocol, such as a transmission control protocol ("TCP") and/or Internet protocol ("IP"). Files can be exchanged between two systems or entities that are capable of receiving image and patient data in DICOM format.

A user interface is used to configure a DICOM data transfer from one device or system to another device or system. For example, a user selects or correlates port information, a DICOM service associated with each port, and other DICOM transfer setup content between devices or systems. A user can input data into fields or utilize a pull down menu of a general user interface.

However, because of terminology as well as complexity of a DICOM transfer, inputting data into the general user interface can be frustrating and complicated. For example, customer administrators or employees may find an unsophisticated or general user interface with only text data fields to be confusing. Such confusion may lead to many errors in configuring a DICOM transfer.

BRIEF SUMMARY

By way of introduction, the preferred embodiments described below include a graphic user interface and/or methods for a DICOM transfer configuration. The graphic user interface is operable to display a visual realization of a DICOM transfer. Image objects of the graphic user interface are operable to be selected to setup or modify a DICOM transfer.

According to a first aspect, a graphic user interface for a digital imaging and communications in medicine ("DICOM") transfer configuration is provided. A first image object corresponding to an origin node is provided. A second image object corresponding to a destination node is provided. The second image object includes an indicator associated with a DICOM transfer. At least one link image object is between the first image object and the second image object. The link image object is indicative of a potential DICOM transfer. The first, second, and link image objects are displayed in a user interface. The potential DICOM transfer is operable to be configured via the user interface.

According to a second aspect, a method for a digital imaging and communications in medicine ("DICOM") transfer configuration is provided. A graphical representation of an origin node is displayed in a user interface. A graphical representation of a destination node is displayed. The graphical representation of the destination node includes an application entity title indicator. At least one graphical representation of a link is displayed between the graphical representation of the origin node and the graphical representation of the destination node. The graphical representation of the link is indicative of a potential DICOM transfer.

According to a third aspect, a computer-readable medium has stored therein instructions executable by a processor in a system for a digital imaging and communications in medicine ("DICOM") transfer configuration. The instructions comprise generating a first icon corresponding to an origin node. A second icon corresponding to a destination node is generated. The first and second icons are in a user interface. At least one link icon between the first image and the second image is generated. The link icon is indicative of a potential DICOM transfer.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

In one example, an origin node and a target or destination node are shown in graphic form in a user interface for configuring a DICOM transfer between the origin and destination nodes. Depending on a type of the destination node, such as an imaging modality or system, printer, workstation, viewing station, PACS device, database, or other device, at least one DICOM service is represented graphically by an arrow or other link image object. Important configuration parameters, such as ports and application entity titles ("AETs"), are portrayed visually with respect to the associated nodes. The graphic user interface simplifies the DICOM configuration and reduces the likelihood of error. Additionally, a test button utilized to test the configured services can be incorporated in the graphic user interface. Also, if an error occurs in the DICOM transfer or transmission, the graphics in the user interface can alert a user of the error, for example, by flashing the arrow or link image object. One may click on or select the flashing arrow or link image object to further troubleshoot the error by reading an error message.

Figure 1:
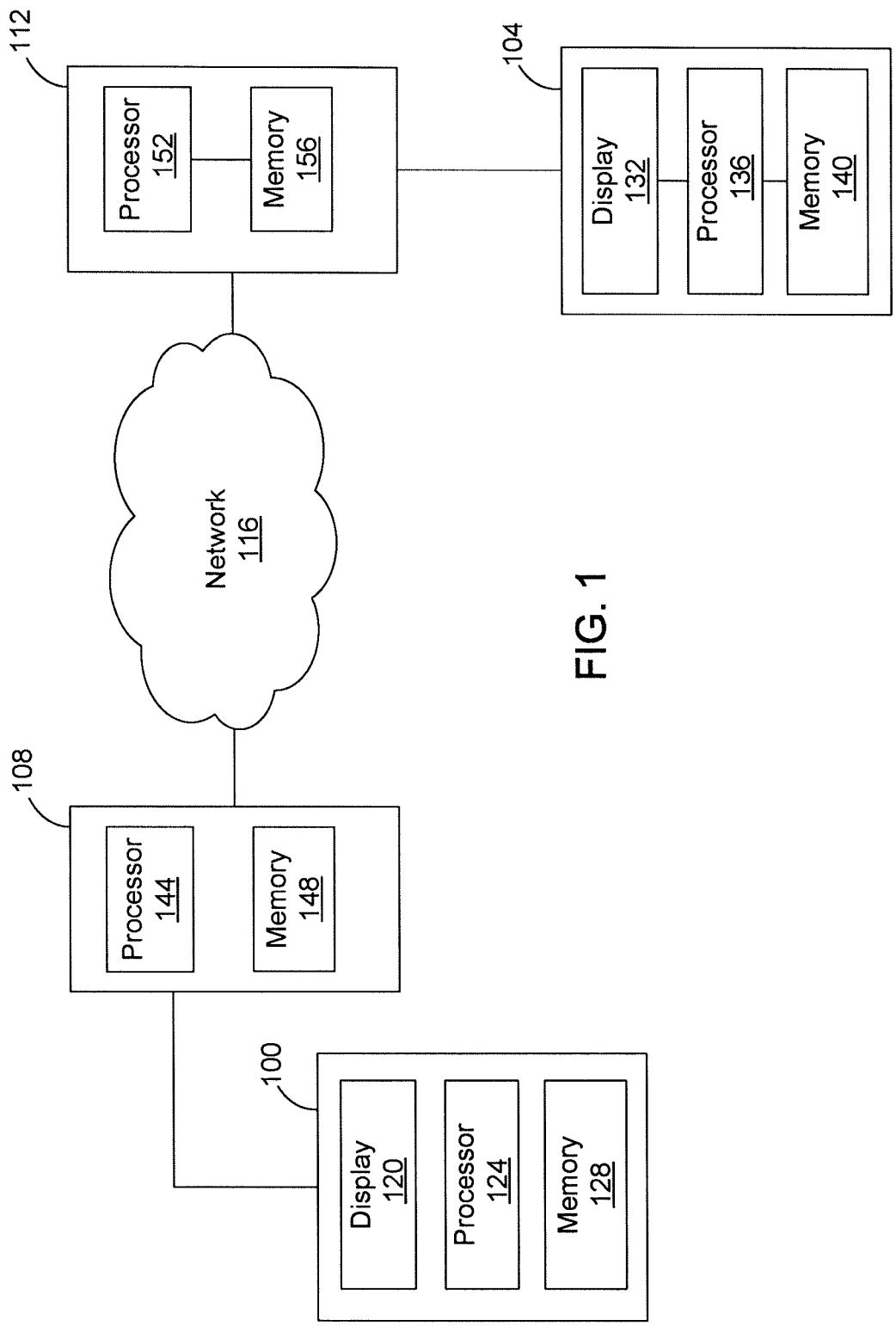
FIG. 1 is a general diagram illustrating one embodiment of a data communication system.

FIG. 1 shows one embodiment of a data communication system. For example, the system is a DICOM system including, but not limited to, a node 100, a node 104, a server 108, a server 112, and a network 116. Additional, different, or fewer components may be provided. For example, a proxy server, a billing server, a router, a switch or intelligent switch, a separate computer or workstation, administrative components, such as an administrative workstation, and/or a gateway device may be provided.

The node 100 is a software application and/or hardware implementation of an imaging modality or system, database or storage file, a workstation, or printer. For example, the node 100 is a magnetic resonance imaging ("MRI") system or scanner, a computed tomography ("CT") system or scanner, an X-ray system or scanner, a workstation, a personal computer, or any other known or future imagining modality. The node 100 includes a display 120, a processor 124, and a memory 128. Additional, different, or fewer components may be provided.

The processor 124 is in communication with the display 120 and the memory 128. The processor 124 may be in communication with more or fewer components. The processor 124 is a general processor, application-specific integrated circuit ("ASIC"), digital signal processor, field programmable gate array ("FPGA"), digital circuit, analog circuit, or combinations thereof. The processor 124 is one or more processors operable to control and/or communicate with the various electronics and logic of the node 100. The processor 124 is operable to execute or run DICOM commands and transfer protocols. The processor 124 is also operable to execute or run applications for image generation.

The display 120 is any mechanical and/or electronic display positioned for accessible viewing in, on, or in communication with the node 100. For example, the display 120 is a touch screen, liquid crystal display ("LCD"), cathode ray tube ("CRT") display, or a plasma display. The memory 128 is any known or future storage device. The memory 128 is one or more non-volatile and/or volatile memories, such as a Random Access Memory "RAM" (electronic), a Read-Only Memory "ROM" (electronic), or an Erasable Programmable Read-Only Memory (EPROM or Flash memory). A memory network may be provided.

The node 100 is operable to communicate with the node 104. For example, the node 100 is operable to transfer or retrieve medical data or content to or from the node 104 via the DICOM standard. The nodes 100 and 104 communicate with each other through the servers 108 and 112 as well as the network 116. Alternatively, the nodes 100 and 104 communicate with each other without the servers 108 and 112 and/or with a different network or connection.

The node 104 is a software application and/or hardware implementation of an imaging modality or system, database or storage file, a workstation, or printer. For example, the node 104 is a magnetic resonance imaging ("MRI") system or scanner, a computed tomography ("CT") system or scanner, an X-ray system or scanner, a workstation, a personal computer, or any other known or future imagining modality. The node 104 includes a display 132, a processor 136, and a memory 140. Additional, different, or fewer components may be provided. For example, the node 104 does not include a display and is utilized for storing or printing data or content.

The processor 136 is in communication with the display 132 and the memory 140. The processor 136 may be in communication with more or fewer components. The processor 136 is similar to or different than the processor 124 and is operable to execute or run DICOM commands and transfer protocols. The processor 136 is also operable to execute or run applications for image generation. The display 132 and the memory 140 are similar to or different than the display 120 and the memory 128, respectively.

The server 108 and/or 112 is a provider server, application server, communications server, database server, proxy server, file server, web server, client server, peer-to-peer server, and/or any known or future server or combinations thereof. Alternatively, the server 108 and/or the server 112 is any other device operable to receive or intercept data or data packets over the network 116. The servers 108 and 112 may be similar or different than each other.

The server 108 and/or 112 is a software and/or hardware implementation. For example, the server 108 and/or 112 is an application program. Alternatively, the server 108 and/or 112 is a server computer or any other hardware that executes and runs server applications. A hardware implementation of the server 108 includes, but is not limited to, a processor 144 and a memory 148, and a hardware implementation of the server 112 includes, but is not limited to, a processor 152 and a memory 156. Additional, different, or fewer components may be provided. The processor 144 is in communication with the memory 148, and the processor 152 is in communication with the memory 156. The processors 144 and 152 may be in communication with more or fewer components.

The processor 144 and/or 152 is a general processor, application-specific integrated circuit ("ASIC"), digital signal processor, field programmable gate array ("FPGA"), digital circuit, analog circuit, or combinations thereof. The processor 144 and/or 152 is one or more processors operable to communicate with electronics of the server 108 and/or 112, respectively, or other components of the system. The memory 148 and/or 156 is any known or future storage device, such as a database or image archival memory. The memory 148 and/or 156 is a non-volatile and/or volatile memory, such as a Random Access Memory "RAM" (electronic), a Read-Only Memory "ROM" (electronic), or an Erasable Programmable Read-Only Memory (EPROM or Flash memory).

The network 116, for example, is any network operable to transfer data or content for the DICOM standard. For example, the network 116 is the Internet, an intranet, a local area network ("LAN"), a wide area network ("WAN"), a virtual private network ("VPN"), and/or any known or future network. Wired and/or wireless connections may be provided. A backbone, network interfaces, network ports, and other network devices may also be provided.

Figure 2:
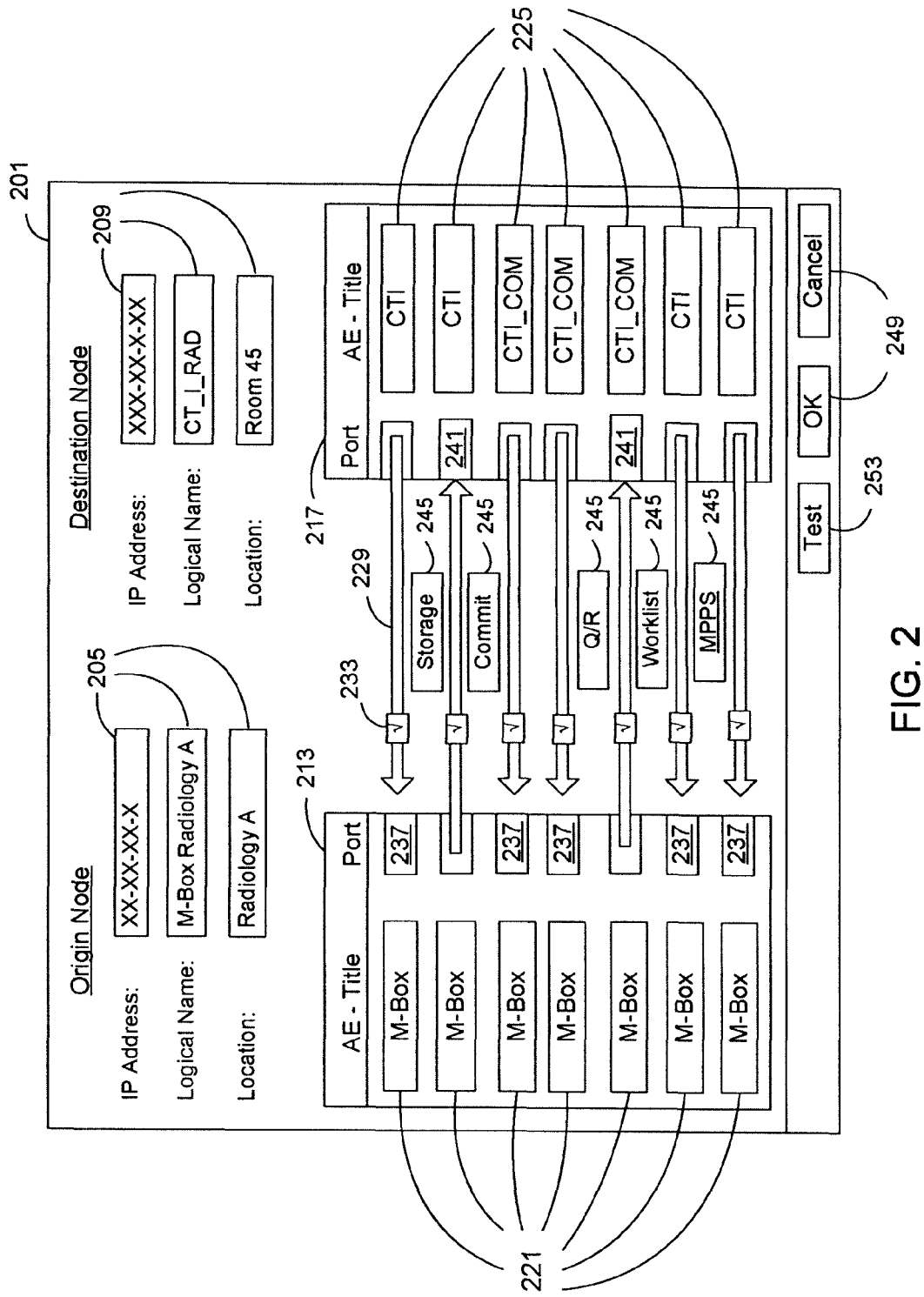
FIG. 2 illustrates one embodiment of a graphic user interface operable to be used in the system of FIG. 1.

FIG. 2 illustrates one embodiment of a graphic user interface operable to be used in the system of FIG. 1. The user interface 201 is displayed on a display associated with a node, such as the display 120, the display 132, or a separate display of an origin node. The user interface 201 includes data indicators 205, data indicators 209, a graphical representation 213 of an origin node, a graphical representation 217 of a destination node, a plurality of link image objects 229, software buttons 249, and a test button 253. Fewer, more, or different features may be provided.

For example, the data indicators 205 are data fields, drop down menus, and/or labels for information regarding the origin node. The information includes an IP address, a logical name, and a location of the origin node. Fewer, more, or different information may be provided. The data indicators 205 are operable to be selected, modified, or updated in the current screen shot of the user interface 201. Alternatively, the data indicators 205 may not be modified or selected in the current screen shot. For example, a user may need to go back to a previous or different screen of the user interface 201 to modify the data of the data indicators 205. The information of the data indicators 205 is automatically inserted and/or updated by the origin node or different device. The information is stored in the origin node. Alternatively, the information is manually inserted by a user of the origin node or separate device.

The data indicators 209 are data fields, drop down menus, and/or labels for information regarding a destination node. The information includes an IP address, a logical name, and a location of the destination node. Fewer, more, or different information may be provided. The data indicators 209 are operable to be selected, modified, or updated in the current screen shot of the user interface 201. Alternatively, the data indicators 209 may not be modified or selected in the current screen shot. For example, a user may need to go back to a previous or different screen of the user interface 201 to modify the data of the data indicators 209. The information of the data indicators 209 is inserted by a user of the origin node. Alternatively, the information is automatically inserted via a remote connection.

The data indicators 205 are visually aligned with the graphical representation 213, and the data indicators 209 are visually aligned with the graphical representation 217. For example, the graphical representation 213 is an image object or icon. The graphical representation 213 includes application entity title ("AET") indicators 221 and port indicators 237. Fewer, more, or different features may be provided. The AET may represent a destination within a node. The AET may also be indicative of potential DICOM services or functions. Also, multiple AETs may correspond to a port. For DICOM transfers, the origin node may utilize one port and one AET. For example, the AET may correspond to a host name. The AET of the origin node is used as an identifier or a confirmation label in a DICOM transfer. Alternatively, the origin node may utilize multiple AETs and/or ports for a DICOM transfer.

The AET indicators 221 and/or the port indicators 237 are operable to be selected, modified, or updated in the current screen shot of the user interface 201. Alternatively, the AET indicators 221 and/or the port indicators 237 may be configured for only viewing in the current screen shot. For example, a user may need to go back to a previous or different screen of the user interface 201 to modify the data of the AET indicators 221 and/or the port indicators 237. The information of the AET indicators 221 and/or the port indicators 237 is automatically inserted or displayed by the origin node. Alternatively, the information is inserted by a user of the origin node or different device.

The graphical representation 217, for example, is an image object or icon. The graphical representation 217 includes application entity title ("AET") indicators 225 and port indicators 241. Fewer, more, or different features may be provided. The AET indicators 225 correspond to one or more AETs or functional destinations of the destination node. The port indicators 241 correspond to the ports allocated or directed to the respective AET. Also, multiple AETs may correspond to a port. For a DICOM transfer, at least one port and at least one AET is defined using the AET indicators 225 and the port indicators 241.

The AET indicators 225 and/or the port indicators 241 are operable to be selected, modified, or updated in the current screen shot of the user interface 201. Alternatively, the AET indicators 225 and/or the port indicators 241 may be configured for only viewing in the current screen shot. For example, a user may need to go back to a previous or different screen of the user interface 201 to modify the data of the AET indicators 225 and/or the port indicators 241. The information of the AET indicators 225 and/or the port indicators 241 is manually inserted by a user of the origin node. For example, a user obtains the information from a conformance statement. Alternatively, the information is automatically inserted or displayed via a remote connection.

The graphic representation 213 and the graphic representation 217 are visually linked via at least one of the plurality of the link image objects 229. The link image objects 229 are icons or graphical representations of a link. For example, the link image objects 229 are image objects of arrows identifying the direction, flow, and/or service of a potential DICOM transfer. For example, the link image objects 229 illustrate potential flow of data for a given DICOM function or service between respective ports of the origin node and the destination node.

The link image objects 229 may include a check box 233 operable to be selected or checked. For example, when configuring a DICOM transfer between the origin node and the destination node, a user can select which functions or services to perform for the DICOM transfer by checking the respective check boxes 233. The link image objects 229 may change color or be shaded or unshaded depending on whether they have been selected or not. Service labels 245 may also be provided on, near, or associated with the link image objects 229. The service labels 245 indicate the functional service to be performed between respective ports and/or AETs. For example, services include, but are not limited to, storage of data, query and retrieve functions, a worklist function, and a reporting function, such as an MPPS function. For example, the worklist function may provide a list of examinations to be performed by the destination node in a day, week, or other time period. The reporting function may provide feedback notifying the origin node about what examinations or procedures have been performed.

Additional link image objects 229 may be associated with a function. For example, for a link image object 229 indicative of file storage, another link image object 229 may be generated or displayed indicating the ability to provide feedback or inform the origin node that storage has been completed.

The link image objects 229 can be selected to further configure the DICOM transfer. For example, at least one of the link image objects 229 is selected or clicked on to define or modify a transfer syntax, such as a type of compression to be used for a DICOM transfer. Furthermore, the link image objects 229 are operable to flash or change color if an error occurs during the DICOM transfer. For example, a flashing link image object 229 is further operable to be selected or clicked on to view an error message for trouble shooting.

The user interface 201 also includes the software buttons 249 and a test button 253. The software buttons 249 are operable to be selected to perform functions to navigate a user through the user interface. For example, the software buttons 249 may perform an OK or Enter function as well as a cancel function. Fewer, more, or different functions may be performed. For example, a previous screen function may be provided. The test button is operable to be selected to test, confirm, and/or verify the selections made for the DICOM transfer. For example, if a user has setup a DICOM transfer to store images in the destination node, the test button can be selected to confirm whether the destination node is operable to store images in a certain compression format. Therefore, default or selected parameters or features are operable to be tested before the DICOM transfer to expedite the configuration.

Figure 3:
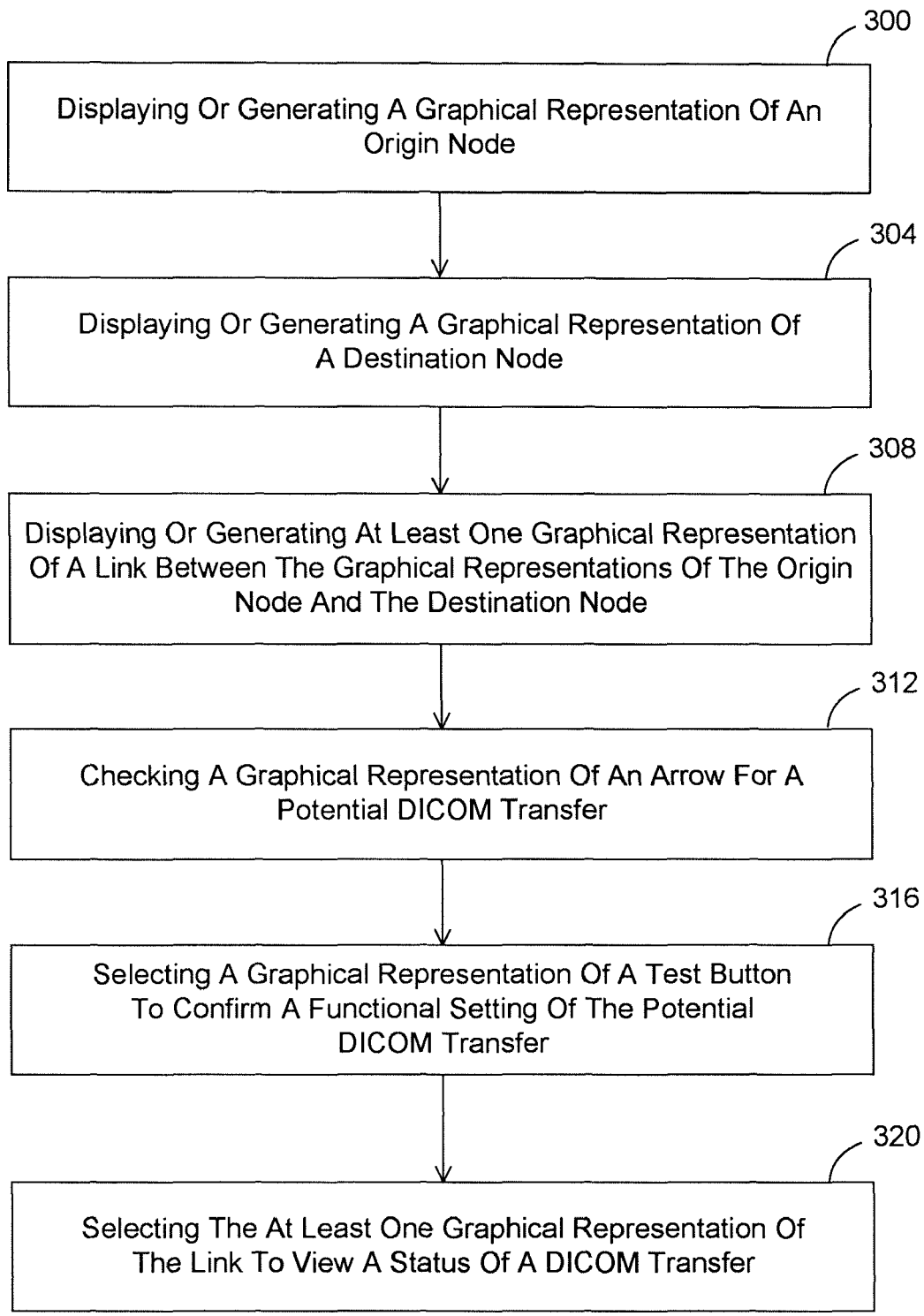
FIG. 3 is a flowchart illustrating one embodiment of a method for configuring a DICOM transfer.

FIG. 3 is a flowchart illustrating one embodiment of a method for configuring a DICOM transfer. Fewer, more, or different acts may be provided. The method is implemented by the system of FIG. 1 or a different system. The method generates and/or uses the user interface of FIG. 2 or another user interface.

For example, a user at an origin node begins or continues to configure a DICOM transfer between the origin node and a destination node using a user interface, such as the user interface 201. The origin node is the node 100 and the destination node is the node 104 or vice versa. Alternatively, different nodes may be used for the origin and/or destination nodes. The user views a screen shot of the user interface to enter or input information of the destination node, such as an IP address, a logical name, a location, and/or any other data related to the data indicators 209. The user may also enter or input AET data or port data, such as data related to the indicators 225 and 241. Alternatively, the configuration data of the destination node is automatically entered or inserted into the user interface.

Information concerning the origin node, such as an IP address, logical name, location, AET, port, and/or data related to the data indicators 205 as well as the indicators 221 and 237 is automatically entered or inserted by the origin node. For example, the origin node configuration data is stored in a memory, such as the memory 128 or the memory 140, and is retrieved for DICOM transfers. Alternatively, the user inputs or enters the origin node configuration data in the user interface.

In act 300, a graphical representation of the origin node, such as the graphical representation 213, is displayed or generated. For example, the configuration data of the origin node is inserted or entered into a screen of the user interface, and the graphical representation of the origin node appears or is generated in a next screen. Alternatively, a default graphical representation of the origin node with empty data fields is generated, and the configuration data is inserted into the data fields in a current screen. The graphical representation of the origin node includes data indicators, such as the AET indicators 221 and port indicators 237.

In act 304, a graphical representation of the destination node, such as the graphical representation 217, is displayed or generated. For example, the configuration data of the destination node is inserted or entered into a screen of the user interface, and the graphical representation of the destination node appears or is generated in a next screen. Alternatively, a default graphical representation of the destination node with empty data fields is generated, and the configuration data is inserted into the data fields in a current screen. The graphical representation of the destination node includes data indicators, such as the AET indicators 225 and port indicators 241. The graphical representation of the destination node may be generated and/or displayed before, after, or substantially at the same time as the graphical representation of the origin node.

In act 308, at least one link image object, such as at least one of the link image objects 229, is displayed or generated between the graphical representation of the origin node and the graphical representation of the destination node. For example, multiple link image objects indicating respective flows of data for a variety of services or functions of a potential DICOM transfer are displayed between respective port indicators of the graphical representations of the origin and destination nodes. For example, the link image objects are images of arrows that are operable to be selected for a DICOM transfer or further configuration. The link image objects may include check boxes or other data fields for selection. The link image objects are automatically generated or displayed substantially at the same time as the generation or display of the graphical representations of the origin and destination nodes. Alternatively, the link image objects may be generated and/or displayed before or after the generation or display of the graphical representation of the origin node and/or the graphical representation of the destination node.

Fewer, more, or different icons, image objects, or graphical representations may be generated or displayed in the user interface. For example, data indicator or fields relating to the IP address, logical name, and/or the location of the respective origin and destination nodes, such as the data indicators 205 and 209, are generated and displayed. These data indicators are aligned with the respective origin node and destination node to allow for easy user recognition of the data. The data indicators are generated or displayed substantially at the same time or at a different time as the generation or display of the graphical representations of the origin and destination nodes. Furthermore, software buttons, such as the software buttons 249 and the test button 253, and service indicators, such as the service labels 254, may be generated or displayed in the user interface. The data indicators, software buttons, and the service labels may be displayed on a same or different screen of the user interface.

In act 312, at least one of the link image objects is checked or selected for a DICOM transfer. For example, after all the configuration data is entered into the user interface and the user is able to view the graphical representation of a potential DICOM transfer, the user selects what functions or services to execute for the DICOM transfer. The user clicks on a check box or associated area or field of a link image object to select a desired service. For example, all possible DICOM services or functions are displayed via the link image objects, and the user selects one or more of the services by checking or selecting the respective link image object. The link image objects that are selected change color or are shaded to indicate selection. Alternatively, the link image objects that are not selected change color or are shaded to indicate non-selection. Or, the link image objects not selected are not displayed in a next screen of the user interface or after a refresh of a current screen.

In act 316, the graphical representation of the test button or the software test button is selected to confirm a functional setting of the potential DICOM transfer. For example, default or selected settings of a DICOM transfer, such as a transfer compression type, are associated with some or all of the DICOM services. A user activates or clicks on the software test button to determine if the settings of each of the selected DICOM services will be accepted for the DICOM transfer. For example, if a user selects a specific compression type for storing a file at the destination node, the activation of the test button will confirm whether the destination node can accept the compression file. A ping message or TCP or IP commands may be utilized for such confirmation.

If the destination node cannot accept the compression file, a notification message will be displayed on the user interface. Alternatively, the link image object related to the file storage service may flash, change color, or show any other indication. The user then may select a different compression level or standard to meet the requirements of the destination node. If the destination node can accept the compression file and all other services have been confirmed to be acceptable, the DICOM transfer is automatically initiated after the activation of the test button. Alternatively, the user interface indicates to the user that the selected services or functions are validly confirmed, and the user may proceed with the DICOM transfer by selecting another software button.

In act 320, at least one of the link image objects is selected to view a status of the DICOM transfer. For example, after the DICOM transfer has been initiated, the user is able to click on or select any of the link image objects to view a report or message regarding the status of the DICOM service. For example, if the user configured a file storage to the destination node, the user clicks on or selects the link image object corresponding to the file storage. A message appears on the user interface reporting the status of the file storage transfer. For example, a message reciting "file stored" or "storing in progress" may be displayed. Also, if there is an error, then the link image object may flash, change color, or show any other indication. For example, if the file could not be stored, the link image object or another associated link image object flashes and the user clicks on the flashing link image object to read or view the error message. Alternatively, the error message is displayed simultaneously with the flashing link image object without selecting or clicking the flashing link image object.

The logic, software or instructions for implementing the processes, methods and/or techniques discussed above are provided on computer-readable storage media or memories or other tangible media, such as a cache, buffer, RAM, removable media, hard drive, other computer readable storage media, or any other tangible media. The tangible media include various types of volatile and nonvolatile storage media. The functions, acts or tasks illustrated in the figures or described herein are executed in response to one or more sets of logic or instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the logic or instructions are stored in a remote location for transfer through a computer network or over telephone lines. In yet other embodiments, the logic or instructions are stored within a given computer, central processing unit ("CPU"), graphics processing unit ("GPU") or system.

Any of the devices, features, methods, and/or techniques described may be mixed and matched to create different systems and methodologies.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. An apparatus comprising:
a processor configured to generate a graphic user interface for a digital imaging and communications in medicine ("DICOM") transfer configuration;
a memory operably connected to the processor, the memory being configured to store configuration data relating to an origin node for a potential DICOM transfer;
a display operably connected to the processor and the memory, the display being configured to display the graphic user interface for the DICOM transfer configuration, the graphic user interface comprising:
a first image object corresponding to the origin node;
a second image object corresponding to a destination node, the second image object including an indicator associated with a DICOM transfer; and
at least one link image object between the first image object and the second image object, the at least one link image object indicative of the potential DICOM transfer between the origin node and the destination node,
wherein the first image object, the second image object, and the at least one link image object are displayed in a user interface, the potential DICOM transfer operable to be configured via the user interface,
wherein the processor is configured to change an appearance of the at least one link image object between the first image object and the second image object when an error in transfer occurs after the potential DICOM transfer is initiated,
wherein the at least one link image connects the first image object and the second image object, and
wherein the at least one link image object is operable to be selected in order to modify a transfer syntax of the DICOM transfer between the first image object and the second image object.

2. The apparatus of claim 1, wherein the indicator associated with the DICOM transfer comprises an application entity title or port indicator.

3. The apparatus of claim 1, wherein at least one of the origin node or the destination node comprises an imaging modality.

4. The apparatus of claim 1, wherein the user interface is associated with the origin node.

5. The apparatus of claim 1, wherein the first image object includes an application entity title or port indicator.

6. The apparatus of claim 1, wherein the at least one link image object is an arrow that illustrates a direction of the potential DICOM transfer.

7. The apparatus of claim 1, wherein the arrow is operable to be checked or selected.

8. The apparatus of claim 1, wherein the link image object is associated with a DICOM function.

9. The apparatus of claim 1, wherein the at least one link image object is operable to flash or change color based on the status of the DICOM transfer.

10. The apparatus of claim 1, wherein the at least one link image object is further operable to be selected to view a message related to the status of the DICOM transfer.

11. The apparatus of claim 1, further comprising:
an image object of a test button, the image object of the test button operable to be selected to confirm a functional setting of the potential DICOM transfer.

12. A method for configuring a digital imaging and communications in medicine ("DICOM") transfer, the method comprising:
displaying a graphical representation of an origin node in a user interface;
displaying a graphical representation of a destination node, the graphical representation of the destination node including an application entity title indicator;
displaying at least one graphical representation of a transfer link between the graphical representation of the origin node and the graphical representation of the destination node, the at least one graphical representation of the transfer link indicative of a potential DICOM transfer;
changing an appearance of the at least one graphical representation of the transfer link between the graphical representation of the origin node and the graphical representation of the destination node when an error occurs after the potential DICOM transfer is initiated; and
selecting the at least one graphical representation of the transfer link to modify a transfer syntax of the DICOM transfer between the graphical representation of the origin node and the graphical representation of the destination node,
wherein the at least one graphical representation of the transfer link is a line or an arrow.

13. The method of claim 12, wherein the destination node comprises an imaging modality, a workstation, a storage file, or a printer.

14. The method of claim 12, wherein displaying the at least one graphical representation of the transfer link comprises displaying the at least one graphical representation of the transfer link on a screen corresponding to the origin node.

15. The method of claim 12, wherein the graphical representation of the origin node includes an application entity title or port indicator.

16. The method of claim 12, wherein the at least one graphical representation of the transfer link is an arrow that illustrates a direction of the potential DICOM transfer.

17. The method of claim 16, further comprising:
checking or selecting the arrow for the potential DICOM transfer.

18. The method of claim 12, further comprising:
selecting the at least one graphical representation of the transfer link to view a status of a DICOM transfer.

19. The method of claim 12, further comprising:
selecting a graphical representation of a test button to confirm a functional setting of the potential DICOM transfer.

20. A non-transitory computer-readable medium having stored therein instructions executable by a processor in a system for configuring a digital imaging and communications in medicine ("DICOM") transfer, the instructions comprising:
generating a first image icon corresponding to an origin node;
generating a second image icon corresponding to a destination node, the first image icon and the second image icon being in a user interface;
generating at least one link icon between the first image icon and the second image icon, the at least one link icon indicative of a potential DICOM transfer;
changing an appearance of the at least one link icon between the first image icon and the second image icon when an error occurs after the potential DICOM transfer is initiated; and
selecting the at least one link icon to modify a transfer syntax of the DICOM transfer between the first image icon and the second image icon,
wherein the at least one link icon is a line or an arrow.

21. The instructions of claim 20, wherein the origin node comprises an imaging modality, a workstation, or a storage file.

22. The instructions of claim 20, wherein generating the at least one link icon comprises displaying an icon of an arrow on a screen corresponding to the origin node.

23. The instructions of claim 20, wherein the second image icon includes an application entity title or port indicator.

* * * * *